United States Patent [19]  
Matsuda et al.

[11] 4,436,917  
[45] Mar. 13, 1984

[54] PROCESS FOR THE PREPARATION OF INDOLES

[75] Inventors: Fujio Matsuda, Kamakura; Takazo Kato, Ashigarakami, both of Japan

[73] Assignee: Mitsui Toatsu Chemicals, Inc., Tokyo, Japan

[21] Appl. No.: 254,310

[22] Filed: Apr. 15, 1981

[51] Int. Cl.$^3$ .................. C07D 209/08; C07D 209/12
[52] U.S. Cl. .................................................... 548/508
[58] Field of Search ...................... 260/319.1; 548/508

[56] References Cited

U.S. PATENT DOCUMENTS 3,699,120 10/1972 Bakke et al. ............... 260/319.1
3,984,434 10/1976 O'Murchu .................. 260/319.1

FOREIGN PATENT DOCUMENTS 50-197608 3/1975 Japan ................. 260/319.1
54-105663 2/1979 Japan ................. 260/319.1
55-108850 8/1980 Japan ................. 260/319.1
56-36451 4/1981 Japan .

OTHER PUBLICATIONS

Chemical Abstracts, 66, 75974s, (1967), pp. 7126–7127.
Chemical Abstracts, 70, 78437n (1969), p. 6.
Ind. Eng. Chem. 43(7), 1579 (1951) Catalytic Reactions of Aromatic Amines, Alkylation with Alcohols, Hill et al.
Chemical Abstracts, 82, P170329z (1975) Governale et al.
J.A.C.S., 101:2, Jan. 17, 1979, "Reactions of Aniline with Olefins Catalyzed by Group 8 Metal Complexes: N-Alkylation and Heterocycle Formation".
"Classification of Catalysts by Reactions," edited by Tarama Laboratory Staff of Kyoto University, Japan, published by Kagaku Kogyo Sha (Chemical Industrial Co.) of Tokyo Japan, pp. 74–76, (Sept. 1, 1971).
J.A.C.S., Heine et al., "The Synthesis of Some N-Arylethylenimines 76, 2503 (1954) p. 2503.
Ind. Eng. Chem., Prod. Res. Dev., vol. 15, No. 3, 1976, Bhattacharyya and Nandi, "Synthesis of N-N-Dimethylaniline from Aniline and Methanol," pp. 201–206.

Primary Examiner—Paul M. Coughlan, Jr.
Assistant Examiner—D. B. Springer
Attorney, Agent, or Firm—Fisher, Christen, & Sabol

[57] ABSTRACT

A process for the preparation of indole and derivatives thereof which comprises reacting an aniline with a 1,2-glycol in the vapor phase, the liquid phase or a mixed vapor-liquid phase. Various solid acids, metals and activated carbon can be used as catalysts for this reaction. The present invention makes it possible to prepare indole and derivatives thereof in a single step by using inexpensive compounds as the starting materials.

18 Claims, No Drawings

PROCESS FOR THE PREPARATION OF INDOLES

BACKGROUND OF THE INVENTION (1) Field of the Invention

This invention relates to a novel process for the preparation of indole and derivatives thereof by reacting an aniline with a 1,2-glycol.

(2) Description of the Prior Art

In the prior art, indole derivatives have long been prepared by the well-known Fischer indole synthesis in which phenylhydrazine is reacted with a compound having an aldehyde group. If the aldehyde compound is other than acetaldehyde, the aforesaid Fischer indole synthesis can be applied to obtain indole derivatives in good yield. However, if the aldehyde compound is acetaldehyde, no reaction that yields indole has been believed to take place. In order to overcome this disadvantage, there has recently been proposed an improved process which comprises reacting phenylhydrazine with acetaldehyde at an elevated temperature of from 300° to 400° C. in the presence of an alumina catalyst (Japanese Patent Laid-Open No. 76864/'73).

This process surely permits the reaction to proceed and brings about the formation of indole, but fails to give a satisfactory yield. Moreover, it is greatly disadvantageous in that the catalyst has so short a life as to become totally inactive after 0.5–1 hour's use.

Indole can also be prepared by another process which comprises reacting o-toluidine with formic acid to form o-methyl-N-formylaniline and then fusing it together with potassium hydroxide. However, it is usually impossible to selectively prepare o-toluidine that is used as the starting material in this process. That is, the p-isomer is always formed in an amount equal to or greater than that of the o-isomer. Thus, treatment of the isomer formed as a by-product poses a serious problem in the case of industrial production. Moreover, the handling of solids as in alkali fusion is troublesome. For these reasons, the aforesaid process cannot be regarded as suitable for industrial purposes.

Furthermore, a number of attempts have been made to synthesize indole from N-β-hydroxyethylamine, but none of them are satisfactory from an industrial point of view. For example, a process which comprises effecting the reaction at 300° C. in the presence of an aluminosilicate catalyst [Zhur. Obschue. Khim., Vol. 24, pp. 671–678 (1954)] gives only a very low yield of indole. A process which comprises heating the reactant together with a molten mixed salt consisting mainly of zinc chloride (Japanese Patent Laid-Open No. 57968/'73) can give a fairly high yield of indole. However, this process has the disadvantage of requiring a complicated procedure, which makes it unsuitable for industrial purposes.

As described above, a number of processes for the synthesis of indole and derivatives thereof have been proposed. However, many of them are disadvantageous in that large amounts of by-products are formed, expensive compounds are used as the starting materials, and/or lengthy and complicated procedures are required to obtain the desired products.

SUMMARY OF THE INVENTION

It is an object of the present invention to provide a one-step process for the highly selective preparation of indole and derivatives thereof by using inexpensive compounds as the starting materials.

According to the present invention, there is provided a process for the preparation of indole and derivatives thereof which comprises reacting an aniline with a 1,2-glycol.

This reaction can be carried out both in the liquid phase and in the vapor phase. By way of example, the process of the present invention makes it possible to obtain indole by reacting aniline with ethylene glycol and to obtain 5-methylindole by reacting p-toluidine with ethylene glycol.

Thus, the process of the present invention has a number of advantages. First, the anilines and 1,2-glycols which can be used as the starting materials are very inexpensive. Secondly, the preparation of indole or a derivative thereof from the starting materials can be achieved in a single step. Thirdly, by-products are scarcely formed and a very high selectivity is attained, so that indole and derivatives thereof can be obtained in highly pure form.

DETAILED DESCRIPTION OF THE INVENTION

The aniline used in the process of the present invention is a compound of the general formula

where R represents a hydrogen atom, halogen atom, hydroxyl group, alkykl group or alkoxy group. Specific examples thereof are aniline, o-toluidine, m-toluidine, p-toluidine, o-haloanilines, p-haloanilines, m-haloanilines, o-aminophenol, m-aminophenol, p-aminophenol, o-anisidine, m-anisidine, p-anisidine and the like.

The 1,2-glycol used in the process of the present invention is a member selected from the group consisting of ethylene glycol, propylene glycol, 1,2-butanediol, 1,2,4-butanetriol, glycerol, 2,3-butanediol, diethylene glycol and the like.

Although the process of the present invention can be carried out in the absence of catalyst, it is preferably carried out in the presence of a solid acid catalyst, a metallic catalyst or activated carbon to obtain the desired product in good yield.

The solid acid catalysts which can be used in the process of the present invention fall under the following three categories:

(1) Catalysts containing an oxide or hydroxide (hereinafter referred to as the catalytic substance (1) of at least one element selected from the group consisting of Si, Al, B, Sb, Bi, Sn, Pb, Ga, Ti, Zr, Be, Mg, Y, Ag, Zn, Cd and the lanthanides. Specific examples of the catalytic substance (1) are CdO, ZnO—Sb$_2$O, PbO$_2$, Al$_2$O$_3$—B$_2$O$_3$, SiO$_2$—CdO, SiO$_2$—Al$_2$O$_3$, SiO$_2$—MgO, TiO$_2$—SnO$_2$, TiO$_2$—ZrO$_2$, CdO—Bi$_2$O$_3$, SiO$_2$—Y$_2$O$_3$, SiO$_2$, Bi$_2$O$_3$—BeO, SiO$_2$—Ga$_2$O$_3$, SiO$_2$—La$_2$O$_3$, SiO$_2$—Ce$_2$O$_3$, SiO$_2$—ZnO—AgO and the like.

(2) Catalysts containing a sulfide or selenide (hereinafter referred to as the catalytic substance (2)) of at least one element selected from the group consisting of Pd, Pt, Cr, Mo and W. Specific examples of the catalytic substance (2) are PdS, PtS, CrS, MoS$_2$, WS$_2$ and the like.

(3) Catalysts containing an inorganic acid salt (hereinafter referred to as the catalytic substance (3)) of at least one element selected from the group consisting of Tl, Mn, Bi, Y, Al, Zn, Cd, In, Ga and the lanthanides. The useful inorganic acid salts include halides, carbonates, nitrates, sulfates, phosphates, pyrophosphates, phosphomolybdates and silicotungstates, and specific examples of the catalytic substance (3) are thallium sulfate, manganese sulfate, bismuth sulfate, yttrium sulfate, cadmium bromide, aluminum sulfate, zinc sulfate, cadmium chloride, indium sulfate, cadmium nitrate, zinc aluminum sulfate, cadmium sulfate, cadmium phosphate and the like.

The metallic catalysts which can be used in the process of the present invention include catalysts containing at least one element (hereinafter referred to as the catalytic substance (4) selected from the group consisting of Ag, Pt, Pd, Ni, Co, Fe, Ir, Os, Ru and Rh.

The solid acid catalysts and metallic catalysts which are usable in the process of the present invention can be prepared by any suitable methods that are known in this field of art. More specifically, solid acid catalysts falling under the category of the catalytic substance (1) can be prepared, for example, by hydrolyzing a water-soluble salt of the principal constituent element of the desired catalyst to form its hydroxide and then drying and calcining the resulting gel, or by pyrolyzing an easily decomposable salt of the principal constituent element of the desired catalyst in air.

Solid acid catalysts falling under the category of the catalytic substance (2) can be prepared, for example, by adding sodium sulfide or potassium selenide to a water-soluble salt of the principal constituent element of the desired catalyst or by contacting the principal constituent element of the desired catalyst or a salt thereof with hydrogen sulfide gas or hydrogen selenide gas.

Metallic catalysts falling under the category of the catalytic substance (4) can be prepared, for example, by reducing a salt, hydroxide or oxide of the principal constituent element of the desired catalyst by mean of a reducing agent such as hydrogen, formalin, formic acid, phosphorous acid, hydrazine or the like.

In the process of the present invention, the above-described catalytic substances (1), (2), (3) and (4) may be used alone or in admixture. Moreover, these catalytic substances and mixtures thereof may be used as such or in the form of supported catalysts. Although any carriers that are in common use for this purpose can be used, diatomaceous earth, pumice, titania, silica-alumina, alumina, magnesia, silica gel, activated carbon, activated clay, asbestos and the like are used in typical cases. Supported catalysts can be prepared by supporting the above-described catalytic substances on these carriers according to any conventional techniques. No particular limitation is placed on the amount of catalytic substance supported on the carrier. Usually, depending on the type of carrier used, any suitable amount (for example, from 1 to 50%) of catalytic substance may be supported thereon.

In addition, various types of activated carbon can be used in the process of the present invention. They include, for example, products made from coconut shell, wood, sawdust, lignin, coal, blood charcoal, bone charcoal, petroleum carbon and the like. They are commercially available in powdered from, in crushed form, or in shaped form (for example, in the shape of globules or cylinders). However, no particular limitation is placed on the form of activated carbon used.

Among the solid acid catalysts falling under the category of the catalytic substance (3), the sulfates and particularly cadmium sulfate are preferred for the purpose of obtaining the desired product in good yield. Among the solid acid catalysts falling under the category of the catalytic substance (2), platinum sulfide and palladium sulfide are particularly preferred. Among the metallic catalysts falling under the category of the catalytic substance (4), Ag is preferred.

Although the process of the present invention can be carried out in the vapor phase, the liquid phase or a mixed vapor-liquid phase, it is usually carried out in the vapor phase. Where the process of the present invention is carried out in the vapor phase, a fixed-bed, fluidized-bed or moving-bed reactor can be used to effect the reaction by heating the vapors of an aniline and a 1,2-glycol in the presence or absence of a catalyst. In this case, various inert gaseous substances may coexist as diluents for the vapors of the starting materials. The useful inert gaseous substances include, for example, nitrogen gas, carbon dioxide gas, water vapor, and the vapors of compounds that are inert to this reaction. Moreover, hydrogen gas or a hydrogen-containing gas may be used as a diluent.

The use of hydrogen gas or a hydrogen-containing gas is especially suitable for the purpose of maintaining the activity of the catalyst.

Similarly, owing to its ability to suppress the decomposition of the 1,2-glycol over the catalyst, the use of water vapor is suitable for the purpose of maintaining the activity of the catalyst and enhancing the yield of the desired product.

The amounts of aniline and 1,2-glycol fed to the reactor should be such that from 0.01 to 5 moles and preferably from 0.05 to 2 moles of the 1,2-glycol is provided for each mole of the aniline. If the amounts are outside this range, a reduction in yield will be caused and/or large amounts of by-products will be formed. These starting materials are fed, after being vaporized in advance or directly in liquid form, to the reactor at a liquid space velocity of from 0.01 to 5 liters/liter of the catalyst/hour.

The process of the present invention is carried out at a reaction temperature in the range of from 200° to 600° C. and preferably from 250° to 500° C. If the reaction temperature is lower than 200° C., the reaction can hardly proceed, while if it is lower than 600° C., undesirably large amounts of by-products will be formed.

The reaction pressure may be superatmospheric, atmospheric or subatmospheric.

Where the process of the present invention is carried out in the liquid phase or a mixed vapor-liquid phase, the reaction is effected by heating a mixture of an aniline and a 1,2-glycol in the presence of at least one member selected from the above-described catalysts. In this case, various inert gaseous substances and/or solvents may coexist as diluents for the starting materials. The useful inert gaseous substances include, for example, nitrogen gas, carbon dioxide gas, water vapor and the vapors of compounds that are inert to this reaction. The useful solvents include, for example, benzene, toluene, xylene, methanol, ethanol, isopropanol, dioxane, dimethylformamide, dimethyl sulfoxide, pyridine, N-methylpyrrolidone trimethylamine, diethylamine, triethylamine, tripropylamine, tributylamine, diphenylamine, triphenylamine and other organic solvents.

In the case of liquid-phase reaction, the process of the present invention can be carried out in a fixed-bed, fluidized-bed or moving-bed reactor or in a rotary or continuous reactor for liquid-phase reactions. However, no particular limitation is placed on the type of reactor used.

The amounts of aniline and 1,2-glycol used as the starting materials for this reaction should be such that from 0.05 to 5 moles and preferably from 0.1 to 2 moles of the 1,2-glycol is provided for each mole of the aniline.

No particular limitation is placed on the amount of catalyst used for this reaction. However, the catalyst is generally used in an amount of from 0.01 to 20 g and preferably from 0.1 to 10 g of the active component thereof per mole of the aniline used as one of the starting materials.

The reaction temperature should be in the range of from 200° to 500° C. and preferably from 250° to 400° C. If the reaction temperature is lower than 200° C., the reaction can hardly proceed, while if it is higher than 500° C., undesirably large amounts of by-products will be formed.

The reaction pressure may be superatmospheric or atmospheric.

In various embodiments of the present invention, indole or a derivative thereof can readily be obtained in pure form by isolating it from the reaction product according to any conventional technique such as distillation.

The present invention is further illustrated by the following examples.

EXAMPLE 1

Cadmium sulfate in powder form was compressed and then crushed to particles. A 10-mm glass flow reactor made of Pyrex was packed with 5 ml of the particles. The front end of this reactor was connected with a feed inlet pipe and a gas inlet pipe to form a feed vaporization zone, while the rear end thereof was connected with a receiver by way of an air-cooling zone.

In the reaction zone, the internal temperature of the reactor was kept at 325° C. Then, a mixture consisting of 1 mole of aniline and 0.02 mole of ethylene glycol was introduced therein through the feed inlet pipe at a liquid space velocity of 0.1 liter/liter of the catalyst/hour. At the same time, nitrogen gas at atmospheric pressure was passed therethrough in an amount of 10 moles per mole of the aniline used as a starting material. After the reaction was carried out for 3 hours, the reaction product withdrawn from the reactor, condensed and collected in the receiver was analyzed by gas chromatography. This revealed that indole was obtained in a 91% yield based on the ethylene glycol and accompanied with very small amounts of by-products.

EXAMPLE 2

The procedure of Example 1 was repeated by using a variety of catalysts. The results thus obtained are summarized in Table 1.

TABLE 1

| Run No. | Catalyst Type | Composition (weight ratio) | Amount Supported on Carrier (% by weight) | Yield of Indole (%) |
|---|---|---|---|---|
| 1. | CdO | — | — | 20 |
| 2. | $Al_2O_3$—$B_2O_3$ | 5:1 | — | 10 |
| 3. | $SiO_2$—CdO | 1:1 | — | 18 |
| 4. | $SiO_2$—ZnO | 1:1 | — | 19 |
| 5. | Zeolite 13X | — | — | 30 |
| 6. | $SiO_2$—MgO | 1:1 | — | 18 |
| 7. | $TiO_2$—$SnO_2$ | 1:1 | — | 13 |
| 8. | CdO—$Bi_2O_3$ | 1:1 | — | 15 |
| 9. | $SiO_2$—$Y_2O_3$ | 1:1 | — | 16 |
| 10. | $SiO_2$ | — | — | 15 |
| 11. | $Bi_2O_3$—BeO | 1:1 | — | 12 |
| 12. | $SiO_2$—$La_2O_3$ | 1:1 | — | 11 |
| 13. | $SiO_2$—$Ce_2O_3$ | 1:1 | — | 12 |
| 14. | $SiO_2$—ZnO—AgO | 1:1:1 | — | 40 |
| 15. | PdS/C | — | 1 | 16 |
| 16. | PtS/C | — | 1 | 25 |
| 17. | FeS | — | — | 38 |
| 18. | $MoS_2$ | — | — | 12 |
| 19. | $Tl_2SO_4$ | — | — | 10 |
| 20. | $MnSO_4 \cdot 4\text{-}6H_2O$ | — | — | 11 |
| 21. | $Y_2(SO_4)_3 \cdot 8H_2O$ | — | — | 13 |
| 22. | $Al_2(SO_4)_3 \cdot 16\text{-}18H_2O$ | — | — | 12 |
| 23. | $ZnSO_4 \cdot 7H_2O$ | — | — | 15 |
| 24. | $CdCl_2 \cdot \frac{1}{2}H_2O$ | — | — | 22 |
| 25. | $In_2(SO_4)_3$ | — | — | 28 |
| 26. | $MgCl_2 \cdot 6H_2O$ | — | — | 42 |
| 27. | $Cd(NO_3)_2$ | — | — | 16 |
| 28. | $Cd_3(PO_4)_2 \cdot 2CdHPO_4$ | — | — | 12 |
| 29. | Ag—$\alpha$-$Al_2O_3$ carrier | — | 10 | 50 |
| 30. | Pt-activated carbon carrier | — | 5 | 36 |
| 31. | Pd-activated carbon carrier | — | 0.5 | 42 |
| 32. | Raney nickel catalyst | — | — | 27 |
| 33. | Raney cobalt catalyst | — | — | 22 |
| 34. | Reduced iron | — | — | 18 |
| 35. | Ir-asbestos carrier | — | 5 | 32 |
| 36. | Os-activated carbon carrier | — | 5 | 34 |
| 37. | Ru-alumina carrier | — | 5 | 38 |
| 38. | Rh-alumina carrier | — | 5 | 43 |
| 39. | Granular activated carbon | — | — | 21 |

EXAMPLE 3

The procedure of Example 1 was repeated except that 5 ml of glass beads having a diameter of 2 mm was used in place of the catalyst of Example 1. As a result, indole was obtained in a 1% yield. Then, the same procedure was repeated once more at a reaction temperature of 500° C. to obtain indole in a 6% yield.

EXAMPLE 4

Using the catalyst of Example 1, reaction was carried out for 27 hours in the same manner as described in Example 1. The reaction mixture collected between the start of the reaction and 3 hours after that (hereinafter referred to as reaction mixture A) and the reaction mixture collected between 24 hours and 27 hours after the start of the reaction (hereinafter referred to as reaction mixture B) were analyzed. This revealed that the yield of indole was 90% for reaction mixture A and 25% for reaction mixture B.

EXAMPLE 5

The procedure of Example 4 was repeated except that hydrogen gas was used in place of the nitrogen gas. This revealed that the yield of indole was 90% for reaction mixture A and 48% for reaction mixture B.

EXAMPLE 6

The procedure of Example 4 was repeated except that a mixed gas consisting of hydrogen gas and water vapor in a molar ratio of 9:1 was used in place of the nitrogen gas. This revealed that the yield of indole increased to 95% for reaction mixture A and 85% for reaction mixture B, thus showing only a slight difference therebetween.

EXAMPLE 7

The procedures of Examples 4, 5 and 6 were repeated by using a catalyst comprising 10% by weight of Ag supported on an $SiO_2$—ZnO carrier (in a weight ratio of 1:1). The results thus obtained are summarized in Table 2.

TABLE 2

| Run No. | Gas Used Type | Molar Ratio | Yield of Indole Reaction Mixture A | Reaction Mixture B |
|---|---|---|---|---|
| 40 | Nitrogen | — | 61% | 30% |
| 41 | Hydrogen | — | 62% | 50% |
| 42 | Hydrogen + water vapor | 9:1 | 71% | 68% |

EXAMPLE 8

The procedure of Example 1 was repeated except that the compounds indicated in Table 3 were used as the starting materials fed to the reactor. The results thus obtained are summarized in Table 3.

TABLE 3

| Run No. | Starting Materials Aniline | 1,2-Glycol | Results Product | Yield |
|---|---|---|---|---|
| 43 | p-Toluidine | Ethylene glycol | 5-Methylindole | 40% |
| 44 | p-Chloroaniline | Ethylene glycol | 5-Chloroindole | 70% |
| 45 | o-Anisidine | Ethylene glycol | 7-Methoxyindole | 32% |
| 46 | Aniline | Propylene glycol | Skatole | 90% |
| 47 | Aniline | 1,2,4-Butanetriol | Triptophol | 12% |

EXAMPLE 9

Into a 200-ml autoclave made of a titanium alloy and fitted with a stirrer were charged with 93.1 g (1 mole) of aniline, 12.4 g (0.2 mole) of ethylene glycol, and 2 g of a palladium-carbon catalyst in powder form (having a Pd content of 0.5% by weight). After the autoclave was purged with nitrogen gas and filled therewith at a pressure of 5 kg/cm$^2$, reaction was carried out at 300° C. for 30 minutes with stirring. After completion of the reaction, the catalyst was separated from the reaction mixture by filtration and the resulting reaction product was analyzed by gas chromatography. This revealed that indole was obtained in a 38% yield based on the ethylene glycol.

EXAMPLE 10

The procedure of Example 9 was repeated except that 1 g of magnesium oxide was used in place of the palladium-carbon catalyst. After completion of the reaction, the magnesium oxide was separated from the reaction mixture by filtration and the resulting reaction product was analyzed by gas chromatography. This revealed that indole was obtained in a 60.7% yield based on the ethylene glycol and accompanied with a small amount of indoline formed as a by-product.

What is claimed is:

1. A process for the preparation of indoles of the formula

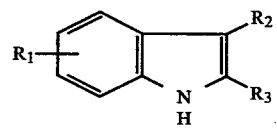

wherein $R_1$ is a hydrogen atom, chlorine atom, bromine atom, methyl group, or methoxy group and $R_2$ and $R_3$ are a hydrogen atom, methyl group or ethyl group, at least one of $R_2$ and $R_3$ being hydrogen which comprises the step of reacting a compound selected from the group consisting of aniline, o-toluidine, m-toluidine, p-toluidine, o-chloroaniline, m-chloroaniline, p-chloroaniline, o-bromoaniline, m-bromoaniline, p-bromoaniline, o-anisidine, m-anisidine or p-anisidine with a member selected from the group consisting of ethylene glycol, propylene glycol, and 1,2-butanediol, in the vapor phase at a temperature of 200° to 600° C., or in the liquid phase or a mixed vapor-liquid phase a temperature of 200° to 500° C. in the presence of a catalytic amount of:

(a) at least one member selected from the group consisting of CdO, $Al_2O_3$—$B_2O_3$, $SiO_2$—CdO, $SiO_2$—MgO, $TiO_2$—$SnO_2$, CdO—$Bi_2O_3$, $SiO_2$—$Y_2O_3$, $Bi_2O_3$—BeO, $SiO_2$—$La_2O_3$, $SiO_2$—$Ce_2O_3$ and $SiO_2$—ZnO—AgO;

(b) a sulfide or selenide of at least one element selected from the group consisting of Pd, Pt, and Mo;

(c) a chloride, nitrate, sulfate or phosphate of at least one element selected from the group consisting of Tl, Mn, Y, Al, Zn, Cd and In;

(d) at least one element selected from the group consisting of Ir, Os and Ru; or (e) Metallic Ag supported on an $\alpha$-$Al_2O_3$ or $SiO_2$—ZnO carrier.

2. A process as claimed in claim 1 wherein the reaction is carried out in the vapor phase at a temperature in the range of from 200° to 600° C.

3. A process as claimed in claim 2 wherein 0.01 to 5 moles of said member selected from the group consisting of ethylene glycol, propylene glycol, and 1,2-butanediol is provided for each mole of said aniline.

4. A process as claimed in claim 1 wherein the reaction is carried out in the liquid phase or a mixed vapor-liquid phase at a temperature in the range of from 200° to 500° C.

5. A process as claimed in claim 4 wherein 0.05 to 5 moles of said member selected from the group consisting of ethylene glycol, propylene glycol, and 1,2 butanediol is provided for each mole of said aniline.

6. A process as claimed in claim 1 wherein the reaction is carried out in the presence of water or water vapor.

7. A process as claimed in claim 1 wherein the reaction is conducted in the presence of a catalytic amount of CdO, Al$_2$O$_3$—B$_2$O$_3$, SiO$_2$—CdO, SiO$_2$—MgO, TiO$_2$—SnO$_2$, CdO—Bi$_2$O$_3$, SiO$_2$—Y$_2$O$_3$, Bi$_2$O$_3$—BeO, SiO$_2$—La$_2$O$_3$, SiO$_2$—Ce$_2$O$_3$, SiO$_2$—ZnO—AgO or a mixture thereof.

8. A process as claimed in claim 1 wherein the reaction is conducted in the presence of a catalytic amount of a sulfide or selenide of at least one element selected from the group consisting of Pd, Pt, and Mo.

9. A process as claimed in claim 1 wherein the reaction is conducted in the presence of a catalytic amount of a chloride, nitrate, sulfate or phosphate of at least one element selected from the group consisting of Tl, Mn, Y, Al, Zn, Cd and In.

10. A process as claimed in claim 8 wherein the catalyst is a sulfate of at least one of said elements.

11. A process as claimed in claim 1 wherein the reaction is conducted in the presence of a catalytic amount of Ir, Os, Ru or a mixture thereof.

12. A process as claimed in claim 1 wherein the reaction is conducted in the presence of a catalytic amount of metallic Ag supported on an α-Al$_2$O$_3$ or SiO$_2$—ZnO carrier.

13. A process as claimed in claim 1 wherein the catalyst or paragraph (b) is a sulfide of at least one element selected from the group consisting of Pd, Pt, and Mo and the catalyst of paragraph (c) is a sulfate of at least one element selected from the group consisting of Tl, Mn, Y, Al, Zn, Cd, and In.

14. A process as claimed in claim 1 wherein indole is prepared.

15. A process for the preparation of indoles which comprises the step of reacting an aniline of the formula

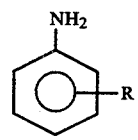

wherein R represents hydrogen, a chlorine atom, methyl group or methoxy group with a glycol selected from the group consisting of ethylene glycol, propylene glycol, and 1,2-butanediol at a temperature of 200° to 600° C. in the vapor phase, or at a temperature of 200° to 500° C. in the liquid phase or a mixed vapor-liquid phase in the presence of a catalytic amount of a member selected from CdO, SiO$_2$—CdO, SiO$_2$—ZnO—AgO, CdSO$_4$, or metallic Ag supported on an α-Al$_2$O$_3$ or SiO$_2$—ZnO carrier.

16. A process as claimed in claim 15 wherein indole is prepared.

17. A process for the preparation of an indole which comprises the step of reacting aniline, p-toluidine, p-chloroaniline or o-anisidine with ethylene glycol, propylene glycol or 1,2-butanediol in the vapor phase at a temperature of 200° to 600° C. in the presence of a catalytic amount of:
(a) at least one member selected from the group consisting of CdO, Al$_2$O$_3$—B$_2$O$_3$, SiO$_2$—CdO, SiO$_2$—MgO, TiO$_2$—SnO$_2$, CdO—Bi$_2$O$_3$, SiO—Y$_2$O$_3$, Bi$_2$O—BeO, SiO$_2$—La$_2$O$_3$, SiO—$_2$—Ce$_2$O$_3$ and SiO2—ZnO—AgO;
(b) a sulfide or selenide of at least one element selected from the group consisting of Pd, Pt and Mo;
(c) a chloride, nitrate, sulfate or phosphate of at least one element selected from the group consisting of Tl, Mn, Y, Al, Zn, Cd and In;
(d) at least one element selected from the group consisting of Ir, Os and Ru; or
(e) metallic Ag supported on an α-Al$_2$O$_3$ or SiO$_2$—ZnO carrier, thereby forming an indole.

18. A process as claimed in claim 1, 7, 8, 17, 11, or 12 wherein the reaction is carried out in an atmosphere of hydrogen gas or a mixture of hydrogen gas and an inert gas.

* * * * *